United States Patent [19]

Dick et al.

[11] 4,167,472

[45] Sep. 11, 1979

[54] HYDROCARBON TREATING PROCESS

[75] Inventors: James E. Dick; Fred T. Sherk; Lewis E. Drehman, all of Bartlesville, Okla.

[73] Assignee: Phillips Petroleum Co., Bartlesville, Okla.

[21] Appl. No.: 900,390

[22] Filed: Apr. 26, 1978

[51] Int. Cl.² .................... C07C 5/40; C07C 15/02; C10G 39/00

[52] U.S. Cl. .................... 208/80; 208/65; 208/78; 208/85; 208/141; 208/310 Z; 585/300; 585/413; 585/418; 585/419

[58] Field of Search ............ 260/673; 208/65, 78, 208/79, 80, 85, 92, 96, 134, 139, 141, 310

[56] References Cited

U.S. PATENT DOCUMENTS

| | | | |
|---|---|---|---|
| 2,891,902 | 6/1959 | Hess et al. | 208/65 |
| 3,007,863 | 11/1961 | Hess et al. | 208/92 |
| 3,461,183 | 8/1969 | Hepp et al. | 260/680 |
| 3,531,543 | 9/1970 | Clippinger et al. | 260/683.3 |
| 3,723,293 | 3/1973 | Glessner et al. | 208/85 |
| 4,000,206 | 12/1976 | Drehman | 260/666 P |

FOREIGN PATENT DOCUMENTS 1295933  11/1972  United Kingdom ............... 260/673.5

Primary Examiner—Delbert E. Gantz
Assistant Examiner—G. E. Schmitkons

[57] ABSTRACT

A process for treating a hydrocarbon composition containing both straight chain and non-straight chain hydrocarbons in which said hydrocarbon composition is separated into a straight chain hydrocarbon-rich fraction and a non-straight chain hydrocarbon-rich fraction, non-aromatics in said non-straight chain hydrocarbon-rich fraction are converted to aromatics, and at least a portion of the straight chain hydrocarbon-rich fraction is passed in combination with steam over a steam active catalyst comprising at least one Group VIII metal and a tin modified Group II metal aluminate under conditions such that aromatics are produced.

19 Claims, 1 Drawing Figure

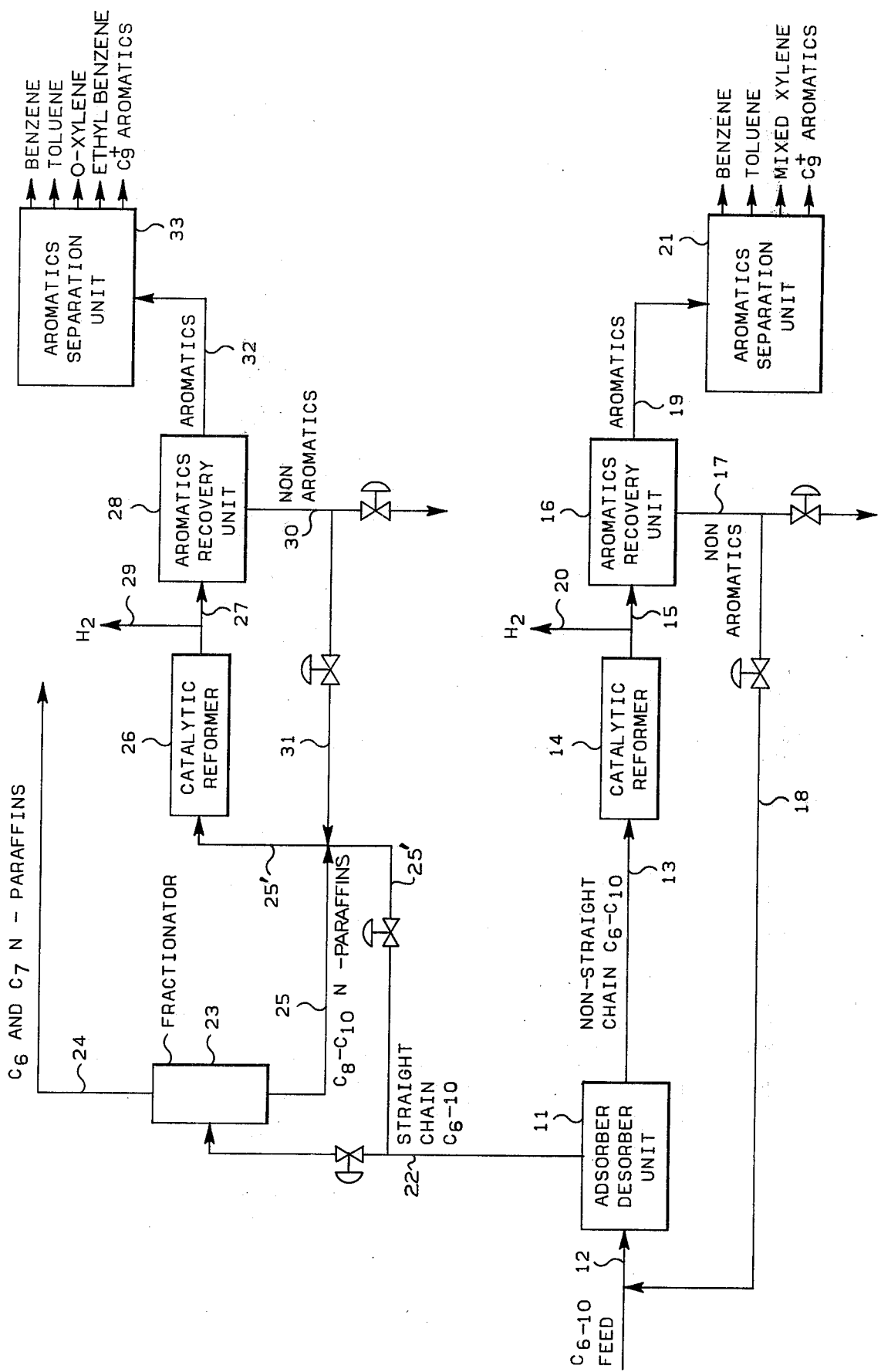

HYDROCARBON TREATING PROCESS

This invention relates to a method of treating hydrocarbons. In one aspect this invention relates to the treating of hydrocarbon fractions such as petroleum fractions or hydrocarbon synthesis fractions (e.g., Fischer-Tropsch fractions). In another aspect this invention relates to the treating of $C_6$–$C_{10}$ hydrocarbon fractions which contain both straight and non-straight chain hydrocarbons.

Many $C_6$–$C_{10}$ hydrocarbon fractions from petroleum fractions or Fischer-Tropsch fractions contain large amounts of compounds that are not of significant value either as motor fuel components or as starting materials for use in profitable chemical processes. In order to convert the low grade $C_6$–$C_{10}$ hydrocarbons into hydrocarbons of more value many different processes have been developed. There is a continuing demand for processes that result in more effective upgrading of such hydrocarbon fractions.

It has been known for some time that the presence of straight chain hydrocarbons reduces the catalyst life of catalysts conventionally used in aromatizing aliphatic hydrocarbon-containing fractions. Accordingly, there have been prior processes in which straight chain hydrocarbons have been removed from a hydrocarbon mixture prior to its being passed into an aromatization zone. The present invention is based upon the discovery that a particular type of steam active catalyst can be used to in turn to aromatize much straight chain hydrocarbons much more efficiently than other aromatization catalysts.

Thus, an object of the present invention is to provide a new process for the treating of hydrocarbon compositions to obtain materials of greater value.

Another object of the present invention is to provide a process providing increased aromatics production over the prior art from hydrocarbon compositions containing both straight and non-straight chain hydrocarbons.

Another object of the present invention is to provide a process for producing a readily separable mixture of ethylbenzene and o-xylene from a hydrocarbon composition containing straight chain and non-straight chain hydrocarbons.

Other objects, aspects and advantages of the present invention will be apparent to those skilled in the art from a study of this detailed description, the appended claims, and the drawings which is a schematic representation of one process embodying the features of the present invention.

In accordance with this invention a hydrocarbon composition containing both straight chain and non-straight chain hydrocarbons is separated into a straight chain hydrocarbon-rich fraction and a non-straight chain hydrocarbon-rich fraction, the non-straight chain hydrocarbon-rich fraction is treated to convert non-aromatics therein to aromatics, and the straight chain hydrocarbon-rich fraction is passed in combination with steam over a steam active catalyst comprising at least one Group VIII metal and a tin modified Group II metal aluminate under conditions such that aromatics are produced.

The separation of the straight chain hydrocarbons from the non-straight hydrocarbons that are processed via a conventional reforming process will result in the conventional reforming process producing more volumes of aromatics per volume of hydrocarbon treated in that reformer. Also it will result in a longer catalyst life for most conventional reforming catalysts. The use of the specified steam active catalyst for reforming the straight chain hydrocarbons will in turn provide an unusually greater amount of aromatics production than other reforming catalysts would provide from such straight chain hydrocarbons.

The term "straight chain hydrocarbon" as used herein is meant to describe aliphatic or acyclic or open chain hydrocarbons which do not possess side branching in the carbon chain. Representative straight chain hydrocarbons include the normal paraffins and the normal olefins including both mono- and polyolefins and straight chain acetylenic hydrocarbons. The non-straight chain hydrocarbons comprise the aromatic and naphthenic hydrocarbons as well as the isoparaffinic and isoolefinic hydrocarbons and the like. The $C_6$–$C_{10}$ naphtha fraction derived from thermal or catalytic cracking is an example of a suitable hydrocarbon mixture for this invention. The present invention is most beneficial for the treating of $C_6$–$C_{10}$ hydrocarbon fractions which contain at least 5 volume percent straight chain hydrocarbons.

Hydrocarbon mixtures can be separated into straight chain and non-straight chain fractions by any suitable means. In one embodiment of this invention any solid selective adsorbent which selectively adsorbs straight chain hydrocarbons to the substantial exclusion of non-straight chain hydrocarbons can be employed. It is preferred, however, to employ as the selective adsorbent certain natural or synthetic zeolites or aluminosilicates, such as a calcium aluminosilicate, or a sodium calcium aluminosilicate, which exhibit the property of a molecular sieve, that is, matter made up of porous crystals wherein the pores of the crystals are of molecular dimension and are of substantially uniform size.

A particularly suitable solid adsorbent for straight chain hydrocarbons is a calcium aluminosilicate, apparently actually a sodium calcium aluminosilicate manufactured by Linde Air Products Company and designated Linde Type 5A molecular sieve. The crystals of this particular calcium aluminosilicate have a pore size or diameter of about 5 Angstrom units, a pore size sufficiently large to admit straight chain hydrocarbons, such as the normal paraffins and normal olefins, to the substantial exclusion of the non-straight chain naphthenic, aromatic, isoparaffinic and isoolefinic hydrocarbons. This particular selective adsorbent is available in various sizes such as ⅛" or 1/16" cylindrical pellets, microspheroids or as a finely divided powder having a particle size in the range 0.5–5.0 microns, exhibiting a bulk density in pounds per cubic foot of 33, and a particle density in grams per cc. of 1.6.

Other suitable solid selective adsorbents include the synthetic and natural zeolites, which, when dehydrated, may be described as crystalline zeolites having a rigid three-dimensional anionic network and having interstitial dimensions sufficiently large to adsorb straight chain hydrocarbons but sufficiently small to exclude non-straight chain hydrocarbons possessing larger molecular dimensions. The naturally occurring zeolite, chabazite, exhibits such desirable properties. Another suitable naturally occurring zeolite is analcite $NaAlSi_2O_6 \cdot H_2O$, which, when dehydrated, and when all or part of the sodium is replaced by an alkaline earth metal, such as calcium, by base exchange yields a material which may be represented by the formula $(Ca, Na_2)$ $Al_2Si_4O_{12}\cdot2H_2O$ and which, after suitable conditioning, will adsorb straight chain hydrocarbons to the substantial exclusion of non-straight chain hydrocarbons. Naturally occurring or synthetically prepared phacolite, gmelinite, harmotome and the like or suitable base exchange modifications of these zeolites are also suitable.

Other solid inorganic or mineral selective adsorbents are known and may be employed in the practice of this invention. It is contemplated that selective adsorbents having the property of selectively adsorbing straight chain hydrocarbons to the substantial exclusion of non-straight chain hydrocarbons in the manner of a molecular sieve may be obtained by suitable treatment of various oxide gels, especially metal oxide gels of the polyvalent amphoteric metal oxides.

The adsorptive separation of the straight chain hydrocarbons from the hydrocarbon fraction undergoing treatment is preferably carried out in the gaseous phase and at any suitable temperature and pressure effective during the adsorptive separation operation to maintain the hydrocarbon fraction undergoing treatment in the vapor phase. For example, the adsorptive separation of the straight chain hydrocarbons by the solid selective adsorbent can be carried out at a temperature in the range 150°–900° F. and at any suitable pressure, such as a pressure in the range 0–2000 psig and higher, the temperature and pressure being adjusted with respect to the hydrocarbon fraction undergoing treatment to maintain the hydrocarbon fraction in the vapor phase.

The regeneration of the selective adsorbent or the desorption of the straight chain hydrocarbons adsorbed in the solid selective adsorbent can be made at any suitable temperature and pressure, preferably at a temperature and pressure such that the resulting desorbed straight chain hydrocarbons are in the vapor phase.

For example, the regeneration-desorption operation may be carried out at a pressure in the range 0–2000 psig or less. Generally a desorption pressure in the range 10–750 psig is suitable. It is sometimes desirable to carry out the desorption operation at a pressure substantially lower than the adsorption pressure. The pressure employed during the adsorptive separation operation is not determinative of the desorption pressure and any suitable desorption pressure may be employed. Substantially the same comment may be made with respect to the desorption temperature in the practice of this invention. It is sometimes desirable, however, to carry out substantially isothermal adsorption-desorption operations. Any suitable desorption temperature in the range 300°–1100° F., higher or lower, may be employed. It is preferred, however, to carry out the regeneration-desorption operation at an elevated temperature, such as a temperature in the range 400°–900° F. or at a temperature at least about 100 degrees Fahrenheit higher than the adsorption temperature, especially in an isobaric adsorption-desorption operation. It is realized, of course, that the desorption temperature should not be excessively high, for example, not greater than about 1100°–1300° F. in the case of Linde Type 5A molecular sieve, since such high temperatures would lead to the destruction of the adsorbent material, presumably by collapse of the crystal structure, with resultant loss of its selective adsorption properties.

Although it is possible to effect desorption of the adsorbed straight chain hydrocarbons from the solid adsorbent by the application of heat alone, for example, by radiant heating, preferably the desorption operation is carried out within a desorption zone in the presence of a gaseous desorbing medium whereby the selective adsorbent undergoing desorption or regeneration is simultaneously selectively desorbed or relieved of the adsorbed straight chain hydrocarbons and carried along or entrained by the gaseous desorbing medium.

As a general rule any suitable gaseous desorbing medium may be employed in the practice of this invention. A suitable gaseous desorbing medium is methane, ethane, propane, natural gas, hydrogen, flue gas, carbon dioxide, carbon monoxide, nitrogen, high-temperature superheated steam, or mixtures thereof. In general, any gaseous or vaporized material chemically inert with respect to the adsorbent and readily separable by fractionation, liquefaction, solvent extraction or adsorption and the like from the desorbed straight chain hydrocarbons is suitable as the desorbing medium in the practice of this invention. It is preferred, however, to employ as the gaseous desorbing medium a hydrogen-containing stream, such as the gaseous hydrogen-containing effluent recovered from a catalytic reforming operation, e.g., the hydrogen-containing effluent from a Platformer. Also preferred as the gaseous desorbing medium is a $C_4$ hydrocarbon fraction, e.g., n-butane and/or isobutane and similar hydrocarbons, including their higher molecular weight homologs, $C_5$ and higher hydrocarbons, which are readily separable as by distillation from the resulting desorbed straight chain hydrocarbons. Preferably an adsorber is employed which will permit adsorption and desorption to be conducted simultaneously. This can be achieved for example by employing two adsorbers or by employing an adsorber of the type described in U.S. Pat. No. 2,891,902 in reference to FIG. 1 of that patent.

A further understanding of the present invention will follow by referring to the FIGURE which is a diagrammatical representation of a preferred method embodying the present invention.

In the process illustrated in the FIGURE a $C_6$–$C_{10}$ hydrocarbon fraction is introduced into an adsorber 11 via line 12. Absorber 11 is operated under suitable conditions of temperature and pressure to effect adsorption of straight chain hydrocarbons from the $C_6$–$C_{10}$ hydrocarbon fraction introduced thereinto with the result that there issues from the adsorber via line 13 an adsorber raffinate richer in non-straight chain hydrocarbons than the original $C_6$–$C_{10}$ hydrocarbon feed. Preferably the adsorber 11 is such that the adsorber raffinate is substantially free of straight chain hydrocarbons. The adsorber raffinate in line 13 is introduced into a catalytic reformer 14 wherein it undergoes catalytic reforming, involving isomerization, dehydrogenation, aromatization, dehydrocyclization, and disproportionation all taking place more or less simultaneously. Catalytic reforming is a well known operation as evidenced by the many commercially available catalytic reforming processes, e.g., Platforming, Ultraforming, Powerforming, Houdriforming, Sovaforming, Catforming and the like. Usually catalytic reforming processes employ an active dehydrogenating platinum-containing catalyst, which catalyst is also effective as an isomerization and dehydrocyclization catalyst. Catalytic reforming is usually carried out at a relatively elevated temperature in the range of about 600° to about 1100° F. (315°–593° C.) and at a relatively elevated pressure in the range of about 100 to 1000 psia (0.69–6.90 MPa) in the presence of recycled hydrogen recovered from the resulting catalytic reformer effluent via line 20. In an especially preferred embodiment the catalytic reformer 14 is a Platformer which is operated with a LHSV (liquid volume of feedstock per volume of catalyst per hour) of adsorber raffinate in the range of 0.5–10 and with about 0.5 to about 10 moles of hydrogen per mole of adsorber raffinate.

The reformate passes from the reformer 14 to an aromatics recovery unit 16 via line 15. Hydrogen and light gases in the reformate are removed via line 20. The aromatics recovery unit may comprise any suitable system involving solvent extraction, extractive distillation, adsorption, and the like, separately or in combination, for the separation of aromatic hydrocarbons. Suitable methods for the removal of aromatic hydrocarbons from non-aromatic hydrocarbons include silica gel adsorption, as exemplified by the Arosorb Process, solvent extraction with a glycol such as diethylene glycol as exemplified by the Udex Process, extractive distillation by contact with a liquid phenol stream or solvent extraction employing liquid furfural, liquid sulfur dioxide, liquid dimethylformamide, Chlorex ($\beta,\beta'$ dichloroethyl ether), sulfolone, and the like. A suitable process for the recovery of aromatic hydrocarbons from a catalytic reformate is known as Rexforming which involves the solvent extraction of a catalytic reformate with a glycol solution for the recovery of high-octane aromatic hydrocarbons as extract.

The non-aromatic hydrocarbons separated are passed from the aromatics recovery unit 16 via line 17 either for recovery for subsequent uses or for recycling partially or totally back to line 12 via line 18 so that the paraffins from the aromatics recovery unit will be recycled through the process.

The aromatics from the aromatics recovery unit 16 in the process illustrated in the FIGURE are passed via line 19 to an aromatics separation unit 21 wherein the aromatics are separated into a benzene fraction, a toluene fraction, a mixed xylene fraction, and a fraction comprising $C_9$ and heavier aromatics. The aromatics separation unit 21 may comprise any fractionator or the like or combination of fractionators suitable for achieving the above-described result.

In one embodiment the desorbed $C_6$–$C_{10}$ straight chain hydrocarbons recovered from the adsorber unit 11 are passed via lines 22 and 25' to a catalytic reformer 26 containing a steam-stable (i.e., steam active) reforming catalyst comprising at least one Group VIII metal or Group VIII metal compound capable of being reduced to a Group VIII metal in combination with a tin-modified Group II metal aluminate, particularly Group II aluminate spinels, preferably zinc aluminate spinel is employed. The term Group II as used herein is intended to denote both Groups IIa and Group IIb.

The Group VIII metals include nickel, platinum, palladium, iridium and osmium, including compounds of such metals which are capable of reduction, e.g., nickel nitrate, and including mixtures thereof. A presently preferred Group VIII metal is platinum.

The Group VIII metal content of the catalyst should be in the approximate range of 0.1 to 5 weight percent, preferably 0.1 to 1 weight percent, of the support.

The tin-modified support material should contain from about 0.01 to about 5 weight percent tin, based on the weight of finished support, preferably from about 0.1 to about 2 weight percent. The tin compound can be added to the support material in a conventional manner such as by deposition from solution, ball mill mixing, volatilization, plasma spraying and the like. The tin compound is incorporated with the support material prior to calcination of the support. Regardless of the manner of preparation, the tin compound must be capable of being converted to either the stannous or stannic oxide form, or to tin metal, per se, as by conversion during calcination. Among the tin compounds which can be employed as the source for the tin or tin oxide in the support compositions are the halides, nitrates, oxalates, acetates, propionates, tartrates, hydroxides, and the like. Subsequent to incorporation of the tin, the resulting intimate mixture is calcined for about 1 to 100 hours at temperatures in the approximate range of 600° to 2500° F. (316°–1371° C.).

In addition to the Group VIII metals, the catalyst composition can include activating components such as alkali metal and alkaline earth metal compounds as well as tin, germanium and lead. The amount of alkali metal or alkaline earth metal is generally within the approximate range of 0.5 to 10 weight percent of the total catalyst. The amount of additional tin will be within the approximate range of 0.1 to 5 weight percent; the amount of germanium or lead will be within the approximate range of 0.1 to 5 weight percent of the total catalyst.

The Group VIII metal compound and, optionally, the adjuvant such as alkali metal, alkaline earth metal, tin, lead or germanium, are applied to the tin-modified support sequentially or simultaneously in a single impregnation procedure. After impregnation the catalyst composites are dried and can be calcined, if desired.

Conditions for the steam-active dehydrocyclization type reformation reaction with such a catalyst are generally about 900° to about 1200° F. (482°–649° C.), preferably about 1020° to about 1120° F. (549°–605° C.), and pressures of about 0 to about 300 psia (0–2.07 MPa), preferably about 40 to about 160 psia (0.276–1.10 MPa). Generally the space velocity of hydrocarbon should be in the range of about 0.5 to about 5 LHSV (liquid volumes per volume of the catalyst per hour). The reaction is carried out in the vapor phase in the presence of steam in the molar ratios of steam to hydrocarbon of about 3:1 to about 30:1, preferably about 5:1 to about 15:1. While the presence of hydrogen is not required, the reforming can be carried out in the presence of up to about 2 moles of hydrogen per mole of hydrocarbon feed.

Now referring back to the diagrammatical representation in the FIGURE, the reformate from the catalytic reformer 26 is passed via line 27 to an aromatics recovery unit 28.

Hydrogen and light gases in the reformate are removed via line 29.

The aromatics recovery unit 28 can comprise any suitable unit as described earlier in reference to aromatics recovery unit 16.

The non-aromatics separated are passed from the aromatics recovery unit 28 via line 20 either for recovery or for recycling partially or totally back to catalytic reformer 26 via line 31 or if desired to catalytic reformer 14 via adsorber 11.

The aromatics from aromatics recovery unit 28 are passed via line 32 to an aromatics separation unit 33 wherein the aromatics are separated into a benzene fraction, a toluene fraction, an o-xylene fraction, an ethylbenzene fraction, and a fraction containing $C_9$ and heavier aromatics. The aromatics separation unit 33 may comprise any fractionator or the like combination of fractionators suitable for achieving the above described result.

An optional embodiment of the present invention which is also illustrated by the FIGURE, the desorbed $C_6$–$C_{10}$ straight chain hydrocarbons recovered from the adsorber unit 11 are passed via line 22 to a fractionator 23 to attain a light fraction of $C_6$–$C_7$ n-paraffins and a heavy fraction of $C_8$–$C_{10}$ n-paraffins. The light fraction passes via line 24 to a suitable point of recovery or to some suitable point for some other use, e.g., such a stream is quite suitable a feedstock for the production of ethylene by cracking.

The heavy fraction of $C_8$–$C_{10}$ n-paraffins is passed via lines 25 and 25' to a catalytic reformer 26.

When the $C_8$–$C_{10}$ n-paraffin stream is primarily $C_8$, which will generally be the case when dealing with a naphtha stream, the reformate will consist mainly of an easily separable mixture of ethylbenzene and o-xylene both of which in high purity are valuable chemical intermediates.

A further understanding of the present invention will be provided by the following examples in which the values employed are typical values based upon actual experimental evaluations.

EXAMPLE I

This example constitutes a control example wherein a naphtha stream is passed through a catalytic reformer of the platforming type and the reformate is passed into an aromatics recovery unit to produce an aromatics stream. With a suitable reformer operated under suitable conditions 39,108 barrels per day of light naphtha can be passed through the reformer to produce the following reformate:

| Benzene | 1,932 BPD (Barrels Per Day) |
|---|---|
| Toluene | 5,487 BPD |
| $C_8$ Aromatics | 5,752 BPD |
| $C_9$ Aromatics | 2,813 BPD |
| Equilibrium Paraffins and Olefins | 13,953 BPD |

Assuming maximum aromatics recovery one would obtain a total aromatics production of 15,984 barrels per day, which is equivalent to about 41% of the volume of the naphtha feed.

EXAMPLE II

This example constitutes yet another control example. In this example the same light naphtha feed used in Example I is passed into a mole sieve unit to produce a $C_6$–$C_9$ straight chain stream and a non-straight chain stream. The straight chain stream and the non-straight chain stream are then passed through separate conventional platformer type reformers to produce separate aromatics containing reformates.

Specifically assume that 53,522 barrels per day of light naphtha is passed through a mole sieve unit to produce 40,463 barrels per day of non-straight chain hydrocarbons and 13,059 barrels per day of straight chain hydrocarbons. The passage of the 40,463 barrels per day of non-straight chain hydrocarbons through one conventional platformer type reformer would produce the following reformate:

| Benzene | 2,450 BPD |
|---|---|
| Toluene | 7,305 BPD |
| $C_8$ Aromatics | 7,428 BPD |
| $C_9$ Aromatics | 3,443 BPD |
| Equilibrium Paraffins | 11,610 BPD |

Thus the total aromatics produced in this first reformer is 20,626 barrels per day.

Since it is known that straight chain hydrocarbons are not converted to aromatics as easily as non-straight chain hydrocarbons, one can readily deduce from the above data regarding the reforming of the non-straight chain hydrocarbons that in Example I the 9,542 barrels per day of straight chain hydrocarbons produced at most about 913 barrels per day of aromatics. Accordingly, it is reasonable to assume that the 13,059 barrels per day of straight chain hydrocarbons of this example when passed through the second conventional platformer would produce no more than about 1,250 barrels per day of aromatics.

Accordingly, the total aromatics yield for such a process would be about 21,876 barrels per day, which is equivalent to about 41% of the volume of the naphtha feed.

EXAMPLE III

This example demonstrates an embodiment of the present invention. A system of the type set forth in the FIGURE is employed. In the system a light naphtha feed is passed into a mole sieve unit 11 to obtain a straight chain $C_6$–$C_9$ stream 22 and a non-straight chain stream 13. The non-straight chain stream is passed to a conventional platformer type reformer 14. The reformate produced in reformer 14 is passed to an aromatics recovery unit 16. The straight chain stream 22 is passed to a steam active catalyst reformer 26 of the type specified in the foregoing claims. The reformate from reformer 26 is then passed to an aromatics recovery unit 28.

A typical material balance in barrels per day for the various relevant lines in such a system is set forth in Table I.

TABLE I

| Components | 12 | 13 | 15 | 19 | 17 | 22 | 25' | 27 | 32 | 30 |
|---|---|---|---|---|---|---|---|---|---|---|
| $C_{6-7}$ n-Paraffins | | | | | | 8,059 | 8,059 | | | |
| $C_{8-9}$ n-Paraffins | | | | | | 5,000 | 5,000 | | | |
| Benzene | | | 2,450 | 2,450 | | | | 1,646 | 1,646 | |
| Toluene | | | 7,305 | 7,305 | | | | 3,004 | 3,004 | |
| $C_8$ Aromatics | | | 7,428 | 7,428 | | | | 2,296 | 2,296 | |
| $C_9$ Aromatics | | | 3,443 | 3,443 | | | | 596 | 596 | |
| Non Straight Chain Hydrocarbons | | 40,463 | | | | | | | | |
| Equilibrium Paraffins & Olefins | | | 11,610 | | 11,610 | | 7,441 | 7,441 | | 7,441 |
| Naphtha | 53,522 | | | | | | | | | |
| Totals | 53,522 | 40,463 | 32,236 | 20,626 | 11,610 | 13,059 | 20,500 | 14,983 | 7,542 | 7,441 |

The total aromatics yield of the system is about 28,168 barrels per day, which is equivalent to about 52.5% of the volume of the naphtha feed. Thus the conversion of the naphtha to aromatics is about 30% better with this inventive system than with the systems set forth in Examples I and II. It can further be noted that for a conventional platformer type reactor of a capacity of about 40,463 barrels per day the total daily aromatics production of this inventive system is about 27% greater than that of the system of Example II and about 71% greater than that of the system of Example I.

EXAMPLE IV

This example demonstrates another embodiment of the present invention. A system of the type set forth in FIG. 1 is again employed. This system differs from that of Example III in that all of the straight chain hydrocarbons are not sent to the catalytic reformer 26. Instead, the straight chain hydrocarbon stream 22 is split into a $C_{8-9}$ stream and a $C_{6-7}$ stream 24. Only the $C_{8-9}$ stream is passed through the catalytic reformer 26. A typical material balance in barrels per day for the various relevant lines in such a system is set forth in Table II.

TABLE II

| Components | 12 | 13 | 15 | 19 | 17 | 22 | 25 | 25' | 27 | 32 | 30 | 24 |
|---|---|---|---|---|---|---|---|---|---|---|---|---|
| $C_{6-7}$ N-Paraffins | | | | | | 8,059 | | | | | | 8,059 |
| $C_{8-9}$ N-Paraffins | | | | | | 5,000 | 5,000 | 5,000 | | | | |
| Benzene | | | 2,450 | 2,450 | | | | | 249 | 249 | | |
| Toluene | | | 7,305 | 7,305 | | | | | 200 | 200 | | |
| $C_8$ Aromatics | | | 7,428 | 7,428 | | | | | 2,122 | 2,122 | | |
| $C_9$ Aromatics | | | 3,443 | 3,443 | | | | | 707 | 707 | | |
| Non Straight Chain Hydrocarbons | | 40,463 | | | | | | | | | | |
| Equilibrium Paraffins & Olefins | | | 11,610 | | 11,610 | | | | 1,370 | 1,370 | 1,370 | |
| Naphtha | 53,522 | | | | | | | | | | | |
| Totals | 53,522 | 40,463 | 32,236 | 20,626 | 11,610 | 13,059 | 5,000 | 6,370 | 4,648 | 3,278 | 1,370 | 8,059 |

The total aromatics yield of the system is about 23,904 barrels per day, which is equivalent to about 45% of the volume of the naphtha feed as compared to 41% for Examples I and II. Also for a conventional platformer type reactor of a capacity of about 40,463 barrels per day, this data illustrates that the total daily production of aromatics with this inventive system is about 9% greater than that of the system of Example II and about 45% greater than that of the system of Example I.

It is also notable that even though significantly less paraffins are passed through reformer 26 in this example the total $C_{8-9}$ aromatics in line 32 of this example are not substantially less than the total $C_{8-9}$ aromatics in line 32 of the system of Example III. Further, it is notable that the ratio of $C_{8-9}$ aromatics to $C_{6-7}$ aromatics in this example is much greater than for the system of Example III. The higher ratio of $C_{8-9}$ aromatics will of course make it easier to subsequently isolate those aromatics in the desired purity from the $C_{6-7}$ aromatics.

It is to be understood that the processes illustrated and described via the FIGURE are just embodiments of the instant invention. Modification of the process illustrated would be within the scope of this invention. For example, if desired the aromatics separation units 21 and 33 could be dispensed with and lines 32 and 19 combined to provide gasoline. Alternatively, the combined stream of lines 19 and 32 could be subjected to fractionation to obtain various aromatic fractions. Also it should be noted that the present invention does not require that the aromatics separation units separate the aromatics into all the product fractions set forth in the description of FIG. 1. Other reasonable variations and modifications, which will be apparent to those skilled in the art, can be made in this invention without departing from the scope and spirit thereof.

What is claimed is:

1. A process for treating a hydrocarbon composition containing both straight chain and non-straight chain hydrocarbons comprising separating said hydrocarbon composition into a straight chain hydrocarbon-rich fraction and a non-straight chain hydrocarbon-rich fraction, converting non-aromatics in said non-straight chain hydrocarbon-rich fraction to aromatics to obtain a first aromatics-containing stream, and passing at least a portion of the straight chain hydrocarbon-rich fraction in combination with steam over a steam active catalyst comprising at least one Group VIII metal and a tin modified Group II metal aluminate under conditions such that a second aromatics-containing stream is produced.

2. A process according to claim 1 wherein said second aromatics-containing stream is separated into a non-aromatics-rich fraction and an aromatics-rich fraction and a non-aromatics-rich fraction is recycled back over said steam active catalyst along with steam under conditions such that aromatics are produced therefrom.

3. A process according to claim 1 wherein said hydrocarbon composition is contacted with a solid adsorbent which selectively adsorbs straight chain hydrocarbons to the substantial exclusion of non-straight chain hydrocarbons to yield as a raffinate said non-straight chain hydrocarbon-rich fraction and wherein the hydrocarbons adsorbed by the solid adsorbent are desorbed to yield as a desorbate said straight chain hydrocarbon-rich fraction.

4. A process according to claim 3, wherein said Group VIII metal is selected from the group consisting of nickel, platinum, palladium, iridium, osmium and mixtures thereof.

5. A process according to claim 4 wherein said Group II metal aluminate is a Group II metal spinel.

6. A process according to claim 5 wherein said Group II metal spinel is zinc aluminate spinel.

7. A process according to claim 6 wherein said tin-modified zinc aluminate spinel contains from about 0.01 to about 5 weight percent tin, based upon the weight of the tin-modified zinc aluminate spinel and said catalyst contains about 0.1 to about 5 weight percent of Group VIII metal based upon the weight of the tin-modified zinc aluminate spinel.

8. A process according to claim 7 wherein the Group VIII metal is platinum.

9. A process according to claim 8 wherein the mole ratio is steam to hydrocarbons passed over said steam active catalyst is in the range of about 3:1 to about 30:1 and wherein the hydrocarbons are passed over said steam active catalyst while in the vapor phase at a temperature in the range of about 900° F. to about 1200° F.

10. A process according to claim 9 wherein said second aromatics-containing stream is separated into a non-aromatics-rich fraction and an aromatics-rich fraction and said non-aromatics-rich fraction is recycled back over said steam active catalyst along with steam under conditions such that more aromatics are produced.

11. A process according to claim 10 wherein said straight chain hydrocarbon-rich fraction is separated into a light fraction rich in $C_6$ and $C_7$ straight chain hydrocarbons and a heavy fraction rich in $C_8-C_{10}$ straight chain hydrocarbons, and only said heavy fraction is passed over said steam active catalyst.

12. A process according to claim 11 wherein the aromatics produced from the $C_8-C_{10}$ straight chain hydrocarbons are separated into a ethylbenzene-rich fraction and an o-xylene-rich fraction.

13. A process according to claim 4 wherein said Group II metal aluminate is zinc aluminate.

14. A process according to claim 13 wherein said tin-modified zinc aluminate contains from about 0.01 to about 5 weight percent tin, based upon the weight of the tin-modified zinc aluminate and said catalyst contains about 0.1 to about 5 weight percent of Group VIII metal based upon the weight of the tin-modified zinc aluminate.

15. A process according to claim 14 wherein the Group VIII metal is platinum.

16. A process according to claim 15 wherein the mole ratio of steam to hydrocarbons passed over said steam active catalyst is in the range of about 3:1 to about 30:1 and wherein the hydrocarbons are passed over said steam active catalyst while in the vapor phase at a temperature in the range of about 900° F. to about 1200° F.

17. A process according to claim 16 wherein said second aromatics-containing stream is separated into a non-aromatics-rich fraction and an aromatics-rich fraction and said non-aromatics-rich fraction is recycled back over said steam active catalyst along with steam under conditions such that more aromatics are produced.

18. A process according to claim 17 wherein said straight chain hydrocarbon-rich fraction is separated into a light fraction rich in $C_6$ and $C_7$ straight chain hydrocarbons and a heavy fraction rich in $C_8-C_{10}$ straight chain hydrocarbons, and only said heavy fraction is passed over said steam active catalyst.

19. A process according to claim 18 wherein the aromatics produced from the $C_8-C_{10}$ straight chain hydrocarbons are separated into a ethylbenzene-rich fraction and an o-xylene-rich fraction.

* * * * *